United States Patent [19]

Lemberger

[11] Patent Number: 5,091,174

[45] Date of Patent: Feb. 25, 1992

[54] PRESERVATIVE FOR BIOLOGICAL SPECIMENS

[76] Inventor: William A. Lemberger, P.O. Box 2482, Oshkosh, Wis. 54903

[21] Appl. No.: 501,382

[22] Filed: Mar. 19, 1990

Related U.S. Application Data

[63] Continuation-in-part of Ser. No. 232,057, Aug. 15, 1988, abandoned.

[51] Int. Cl.$^5$ .......................... A01N 1/00; A01N 59/06
[52] U.S. Cl. ........................................ 424/75; 424/698; 422/1
[58] Field of Search ...................... 424/75, 698; 422/1

[56] References Cited

U.S. PATENT DOCUMENTS 3,573,082  3/1971  Fremling ........................... 424/75 X
4,121,944  10/1978  VanLandingham .............. 424/75 X

*Primary Examiner*—Thurman K. Page
*Assistant Examiner*—G. S. Kishore
*Attorney, Agent, or Firm*—Wheeler Law Firm

[57] ABSTRACT

An embalming fluid. A chemical composition comprising chemicals that are, generally, non-hazardous to humans in the concentrations used. Also, specimens preserved in the composition look and feel more lifelike than specimens preserved in formaldehyde based compositions.

6 Claims, No Drawings

PRESERVATIVE FOR BIOLOGICAL SPECIMENS

This application is a continuation-in-part of Ser. No. 07/232,057 filed on Aug. 15, 1988 which is abandoned.

BACKGROUND OF THE INVENTION

Biological specimens are used every day for the purposes of education. The present invention relates generally to the field of biological specimens and specifically to the field of the preservation of dead biological specimens for the purpose of study and dissection.

In order to preserve the specimens embalming fluid is used. Many different chemicals are used, because of their preservative effects, for embalming fluids. For most of the nineteenth century arsenical compounds were used. However, the use of these compounds was restricted due to the dangers they presented to the living people who would be exposed to them.

Today, a different problem occurs with formaldehyde. Formaldehyde is a very good preservative, however, it tends to cause changes in the specimens that render them less life-like. Some companies attempt to avoid this problem by trying to wash the formaldehyde out of the specimens before they are shipped. This leaves the specimens slightly more life-like. However, washing the specimens does not remove all the formaldehyde from them. Also, because a great deal of the formaldehyde is removed, the specimen is more vulnerable to biological damage; like decay. The present invention is a totally new preservative formula based largely upon chemicals which are approved for use in foods. Therefore, the formula is believed safe for both the persons who prepare the specimens and the persons who use the specimens. In addition, there is an unexpected advantage, the specimens are much more life-like both in color and texture than those prepared in formaldehyde. For that reason they are much better for instructional purposes then specimens preserved in formaldehyde.

A number of preservative that do not contain formaldehyde are known to the inventor. See for example, U.S. Pat. Nos. 3,257,279 (Schain); 3,546,334 (Lerner); 3,624,197 (Schain); 3,837,979 (brown); 4,164,393 (Drury); 4,727,571 (Romero-Sierra et al.); 4,287,222 (Robinson); 4,278,715 (Romero-Sierra et al.); 4,328,256 (Romero-Sierra et al.); 4,349,580 (Romero-Sierra et al.); 4,463,117 (Maline). However, none of the above compositions make use of the same composition of chemicals as in the present invention to achieve their preservative effects. Also, none of the prior art compositions is for the specific purpose of preserving biological specimens for both study and dissection. For example, U.S. Pat. No. 3,837,979 (Brown) claims a method for suspending specimens in a stable, continuous gel whereby the specimen may be observed as it is held immobile in the transparent gel. U.S. Pat. No. 4,463,117 (Maline) shows a process with a result similar to the Brown patent but a different procedure is used. The remaining patents disclose compositions used to preserve animal hides, to preserve plants or plant tissue, and for the preparation of slides for the purpose of microscopic study.

No prior art is known to the inventor which replaces formaldehyde as a preservative for the preparation of biological specimens to be studied and/or dissected.

SUMMARY OF THE INVENTION

The present invention is a mixture of unique composition containing hydantoin, Dowacil 75, methyl paraben, propylparaben neo cebitate vitamin C, an anti-oxidant and aluminum sulfate. Isopropyl alcohol and ethylene glycol or equivalent tissue penetrative compound like propylene glycol or glycerol is used to put the paraben in solution. The resulting solution is used to preserve the biological specimen.

Each component used in making the composition, with the exception of the ethylene glycol and isopropyl alcohol, has been approved as a food additive. The concentrations of each component of the composition, again with the exception of the ethylene glycol and isopropyl alcohol, are at or below the approved level for use as a food additive. Furthermore, the levels of ethylene glycol and isopropyl alcohol used are believed safe for topical applications. However, glycerol or proplyene glycol may be substituted for ethylene glycol to even further increase the safety of the solution. Because they are believed safe for topical use they are believed safe for preparation of specimens that are to be handled and dissected.

The specimens that are preserved in this composition remain more life-like and flexible than specimens preserved in formaldehyde compositions. These and other benefits of the present invention will be apparent from the following description.

DETAILED DESCRIPTION

Although the disclosure hereof is detailed and exact to enable those skilled in the art to practice the invention, the physical embodiments herein disclosed merely exemplify the invention which may be embodied in other specific structure. While the preferred embodiment has been described, the details may be changed without departing from the invention, which is defined by the claims.

To make 190 liters (50 gallons) of the preservative composition the following formula is used:
- 0.24% Dowacil 75—1 lb. (454 g)
- 5% isopropyl alcohol—12 quarts 12 oz. (12.1 liters)
- 5% ethylene glycol or propylene glycol—9 quarts (8.5 liters)
- propyl paraben—1 lbs. 8 oz. (681 g), methyl paraben—4 lbs. 2 oz. (1892 g)
- 1% neo-cebitate (vitamin C)—4 lbs. 2 oz. (1892 g)
- 0.24% commercial alum—1 lb. (454 g)
- 1 quart DMDM Hydantoin Two separate solutions are prepared using the above ingredients:
- A. The parabens are dissolved in the isopropyl alcohol and ethylene or propylene glycol
- B. The Dowacil, neo-cebitate, alum, and DMDM hydantoin are dissolved in water (for example, 25 gallons of water)

Combine the two solutions (A and B) and add enough water to make 50 gallons. If any material does not dissolve, simply use the solution above the precipitate and discard the undissolved material.

It should be noted that in the above formulation the active ingredient in Dowacil 75, a commercial tradename, is 1-(3-chlorloallyl)-3,5,7-triaza-1-azioniaadamaztane chloride. Specifically, the 1-(3-chlorolallyl)-3,5,7-triaza-1-azioniaadamaztane chloride comprises 67.5% of the Dowacil 75 with the rest being inert ingredients. Also, the commercial alum listed in the above formulation is generally a metal sulfate; the most common is potassium aluminum sulfate. Finally, the ethylene glycol, in addition to helping put the methyl paraben into solution, aids the ability of the preservative solution to penetrate the tissue of the specimen quickly and effectively.

The above described embodiments of this invention are merely descriptive of its principles and are not to be limiting. The scope of this invention instead shall be determined from the scope of the following claims, including their equivalents.

What is claimed is:

1. A composition for preserving tissue of biological specimens, said composition comprising:
   an effective amount of at least one anti-fungal and anti-bacteriological paraben preservative selected from the group consisting of methyl paraben, ethyl paraben, propyl paraben, or butyl paraben;
   a sufficient amount of at least one alcohol, approved for topical use and capable of use as a preservative, and a sufficient amount of tissue penetrating means for penetrating the tissue of the biological specimens in which said anti-fungal and anti-bacteriological paraben preservative may be put into solution;
   an effective amount of hydantoin to act as a softening and lubricating agent for softening and lubricating the tissue of the biological specimens;
   an effective amount of 1-(3-chlorolallyl)-3,5,7-triaza-1-azioniaadamaztane chloride to act as an anti-fungal and an anti-biological preservative;
   an effective amount of vitamin C to act as an anti-oxidant;
   an effective amount of at least one alum to act as an astringent;
   a sufficient amount of water for mixing above ingredients whereby a solution results that may be used to preserve biological specimens.

2. The composition of claim 1 in which the alcohol is isopropyl alcohol.

3. The composition of claim 1 in which said alum is potassium aluminum sulfate.

4. The composition of claim 1 comprising a substantially saturated solution.

5. The composition of claim 1 in which the tissue penetrating means is selected from a group consisting of: propylene glycol, ethylene glycol, or glycerol.

6. A composition for preserving tissue of biological specimens, said composition comprising:
   454 grams of 0.24% a mixture containing 65.5% 1-(3-chlorolallyl)-3,5,7-triaza-1-azioniaadamaztane chloride and 32.5% inert ingredients;
   12.1 liters of 5% isopropyl alcohol;
   8.5 liters of propylene glycol;
   681 grams of propyl paraben;
   1892 grams of methyl paraben;
   1892 grams of 1% a mixture of vitamin C;
   454 grams of 0.24% potassium aluminum sulfate;
   0.95 liters of hydantoin;
   said methyl paraben and said propyl paraben being dissolved in said isopropyl alcohol and said propylene glycol so that a paraben solution is formed;
   said Dowacil, said neo-cebitate, said potassium aluminium sulfate, and said hydantoin being mixed with said paraben solution and sufficient water to make 190 liters of the composition being added to the mixture of the two solutions;
   whereby the composition may be used to preserve biological specimens, said propylene glycol enhancing the penetration of said solution into said tissues of said specimens.

* * * * *